US006258960B1

(12) United States Patent
Antilla et al.

(10) Patent No.: US 6,258,960 B1
(45) Date of Patent: Jul. 10, 2001

(54) CATALYTIC ASYMMETRIC SYNTHESIS OF CHIRAL AZIRIDINES

(75) Inventors: Jon Antilla, Somerville, MA (US); William D. Wulff, Okemos, MI (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 09/528,206

(22) Filed: Mar. 17, 2000

(51) Int. Cl.$^7$ ............................. C07D 203/02; C07F 5/02

(52) U.S. Cl. ............................. 548/962; 548/966; 568/6

(58) Field of Search .................................. 548/962, 966; 568/6

(56) References Cited

U.S. PATENT DOCUMENTS 5,053,546 * 10/1991 Kaufman .................................. 568/4

FOREIGN PATENT DOCUMENTS

WO 98/51666    11/1998   (WO) .

OTHER PUBLICATIONS

Antilla et al., "Catalytic Asymmetric Aziridination with a Chiral VAPOL–Boron Lewis Acid", J. Am. Chem. Soc., 121, 5099–5100, Jun. 1999.*
Heller, Goldberg, Yeung, Grant and Wulff, New twists in the reactions of chemzymes, Spring Innovations Limited, Proceedings of the Chiral Europe '97 Symposium, 1997, 19–22.
Osborn and Sweeney, The asymmetric synthesis of aziridines, Tetrahedron: Asymmetry, 1997, 8(11):1693–1715.
David Tanner, Chiral Aziridines—Their Synthesis and Use in Stereoselective Transformations, Agnew Chem. Int. Ed. Engl., 1994, 33:599–619.
Evans, Woerpel, Hinman and Faul, Bis(oxazolines) as Chiral Ligands in Metal–Catalyzed Asymmetric Reactions. Catalytic, Asymmetric Cyclopropanation of Olefins, J. Am. Chem. Soc. 1991, 113:726–728.
Lowenthal and Masamune, Asymmetric Copper–Catalyzed Cyclopropanation of Trisubstituted and Unsymmetrical cis–1,2–Disubstituted Olefins: Modified Bix–Oxazoline Ligands, Tetrahedron Letters, 1991, 32(50):7373–7376.
Li, Conser and Jacobsen, Asymmetric Alkene Aziridination with Readily Available Chiral Diimine–Based Catalysts, J. Am. Chem. Soc. 1993, 115:5326–5327.
Evans, Faul, Bilodeau, Anderson and Barnes, Bis(oxazoline)—Copper Complexes as Chiral Catalysts for the Enantioselective Aziridination of Olefins, J. Am. Chem. Soc. 1993, 115:5328–5329.
Noda, Hosoya, Irie, Ito and Katsuki, Asymmetric Aziridination by Using Optically Active (Salen)manganese(III) Complexes, Synlett, Jul. 1993, 469–471.
Evans, Faul and Bilodeau, Development of the Copper-–Catalyzed Olefin Aziridination Reaction, J. Am. Chem. Soc. 1994, 116:2742–2753.

Tanner, Andersson, Harden and Somfal, $C_2$–Symmetric Bis(Aziridines): A New Class of Chiral Ligands for Transition, Tetrahedron Letters, 1994, 35(26):4631–4634.
Nishikori and Katsuki, Catalytic and Highly Enantioselective Aziridination of Styrene Derivatives, Tetrahedron Letters, 1996, 37(51):9245–9248.
Li, Quan and Jacobsen, Mechanism of the (Dimine) Copper Catalyzed Asymmetric Aziridinationof Alkenes. Nitrene Transfer via Ligand–Accelerated Catalyst, J. Am. Chem. Soc., 1995, 117:589–5890.
Harm, Knight and Stemp, New Tartrate–Derived Bis–Oxazoline Ligands for Enantioselective Cyclopropanation and Aziridination of Alkenes, Synlett, Jul. 1996, 677–678.
Muller, Baud, Jacquier, Moran and Nageli, Review Commentary: Rhodium (II)–Catalyzed Aziridinations and CH Insertions with [N–(p–Nitrobenzenesulfonyl)Imino] Phenyliodinane, Journal of Physical Organic Chemistry, 1996, 9:341–347.
Lai, Kwong, Che and Peng, Catalytic and Asymmetric Aziridination of Alkenes Catalysed By A Chiral Manganese Porphyrin Complex, Chem. Commun., 1997, 2373–2374.
Sodergren, Alonso and Andersson, Readily available nitrene precursors increases the scope of Evans' asymmetric aziridination of olefins, Tetrahedron: Asymmetry, 1997, 8(21):3563–3565.
Hansen, Finney and Jacobsen, Carbenoid Transfer to Imines: A New Asymmetric Catalytic Synthesis of Aziridines, Angew. Chem. Int. Ed. Engl., 1995, 34(6):676–677.
Rasmussen and Jorgensen, Catalytic Formation of Aziridines from Imines and Diazoacetate, J. Chem. Soc., Chem. Commun., 1995, 1401–1402.
Aggarwal, Thompson, Jones and Standen, Novel Catalytic and Asymmetric Process for Aziridination Mediated by Sulfur Ylides, J. Org. Chem, 1996, 61:8368–8369.

(List continued on next page.)

*Primary Examiner*—Fiona T. Powers
(74) *Attorney, Agent, or Firm*—Brinks Hofer Gilson & Lione

(57) ABSTRACT

The present invention relates to the synthesis of chiral cis-aziridines (IIIa and IIIb) by reacting an imine (I) with a diazo compound (II) in the presence of a chiral vaulted biary-Lewis Acid complex as shown below:

20 Claims, No Drawings

OTHER PUBLICATIONS

Casarrubios, Perez, Brookhart and Templeton, Lewis Acid–Catalyzed Synthesis of Aziridines, J. Org. Chem, 1996, 61:8358–8359.

Ha, Kang, Suh and Ahn, A New Synthesis of Aziridine–2–carboxylates by Reaction of Hexahydro–1,3, 5–triazinnes with Alkyldiazoacetates in the Presence of Tin(IV) Chloride, Tetrahedron Letters, 1996, 37(39):7069–7070.

Rasmussen and Jorgensen, Metal–catalysed reactions of imines with ethyl diazoacetate leading to aziridines, J. Chem. Soc., Perkin Trans. 1, 1997, 1287–1291.

Aires–de–Sousa, Lobo and Prabhakar, A New Enantioselective Synthesis of N–Arylaziridines by Phase–Transfer Catalysis, Tetrahedron Letters, 1996, 37(18):3183–3186.

Verstappen, Ariaans and Zwanenburg, Asymmetric Synthesis of 2H–Azirine Carboxylic Esters by an Alkaloid–Mediated Neber Reaction, J. Am. Chem. Soc., 1996, 118:8491–8492.

Bao and Wulff, Vaulted Biaryls as Chiral Ligands for Asymmetric Catalytic Diels–Alder Reactions, J. Am. Chem. Soc., 1993, 115:3814–3815.

Bao and Wulff, A Comparison of Diels–Alder Catalysts Generated from Linear and Vaulted Biaryls and Bromoborane–Dimethylsulfide Complex., Tetrahedron Letters, 1995, 36(19):3321–3324.

Bao, Wulff, Dominy, Fumo, Grant, Rob, Whitcomb, Yeung, Ostrander and Rheingold, Synthesis, Resolution, and Determination of Absolute Configuration of a Vaulted 2,2'Binaphthol and a Vaulted 3,3'–Biphenanthrol (VAPOL), J. Am. Chem. Soc., 1996, 118:3392–3405.

Heller, Goldberg and Wulff, Positive Cooperativity of Product Mimics in the Asymmetric Autoinduction of Diels—Alder Reactions Catalyzed by a VAPOL—Aluminum Catalyst, J. Am. Chem. Soc., 1997, 119:10551–10552.

O'Connor, Ernst, Schoenborn and Holm, Diastereoisomeric Four–Coordinate Complexes. IV. Zinc(II) Complexes with Three Asymmetric Centers and Ligand Racemization in Bis[N–(alkoxycarbonylalkyl)–salicylaldimino] metal(II) complexes, J. Am. Chem. Soc., 1968, 90(7), 1744–1752.

Arnesto, Ortiz and Perez–Ossorio, Aroylation of Carbanions Derived from N–(Diphenylmethyl)arylmethanimines. A Synthesis of 4–Aroyloxy–2–azabuta–1,3–dienes, J. Chem. Soc. Perkin Trans. I, 1986, 2021–2025.

Cainelli, Giacomini, Trere and Boyl, Efficient Transamination under Mild Conditions: Preparation of Primary Amine Derivatives from Carbonyl Compounds via Imine Isomerization with Catalytic Amounts of Potassium tert–Butoxide, J. Org. Chem. 1996, 61:5134–5139.

Green, Patel, Elgendy, Baban, Claeson, Kakkar and Deadman, The Synthesis of 1–Aminobenzylphosphonic acids from Benzylidenediphenylmethylamines, for use as structural units in Antithrombotic tripeptides, Tetrahedron, 1994, 50(17):5099–5108.

Ishihara, Miyata, Hattori, Tada and Yamamoto, A New Chiral BLA Promoter for Asymmetric Aza Diels—Alder and Aldol–Type Reactions of Imines, J. Am. Chem. Soc. 1994, 116:10520–15024.

Lopez, Moreno–Manas, Pleixats and Roglans, Ethyl N–(Diphenylmethylene) glycinate as Anionic Glycine Equivalent. Monoalkylation, Dialkylation and Michael Additions under Solid–Liquid Phase–Transfer Catalysis, Tetrahedron, 52(24):8365–8366/.

Antilla, Wulff, Catalytic Asymmetric Aziridination with a Chiral VAPOL–Boron Lewis Acid, J. Am. Chem. Soc., Feb. 16, 1999.

Antilla, Wulff, Supplementary Material for Catalytic Asymmetric Aziridination with a Chiral VAPOL–Boron Lewis Acid, no date available.

"Metal–catalyzed reactions of imines with ethyl diazoacetate leading to aziridines", K.G. Rasmussen et al., Dept. of Chemistry, Aarhus University, DK–8000 Aarhus C, Denmark, J. Chem. Soc., Perkin Trans 1, 1997, pp. 1287–1291.

* cited by examiner

CATALYTIC ASYMMETRIC SYNTHESIS OF CHIRAL AZIRIDINES

STATEMENT OF GOVERNMENT INTEREST

This invention was made, in part, with Government support awarded by the National Institutes of Health (Grant No. GM 33589).

BACKGROUND OF THE INVENTION

The present invention relates to the synthesis of chiral cis-aziridines (III) by reacting an imine (I) with a diazo compound (II) in the presence of a chiral vaulted biaryl-Lewis Acid complex.

Aziridines are versatile intermediates that have great value in organic synthesis.[1] A recent review on the asymmetric synthesis of aziridines reveals that nearly all non-racemic aziridines are made from other chiral materials.[2] Therefore, there is a need for the development of new methods for the asymmetric catalytic synthesis of aziridines.

Previous reports have focused on three different strategies to this problem. Most past effort has involved the transfer of a nitrene from [N-(p-toluenesulfonyl)imino]phenyl iodinane to an alkene mediated by a chiral metal catalyst which can result in the production of N-tosyl aziridines in good asymmetric inductions with certain alkene substrates.[3] An alternate method involves the transfer of a carbene to an imine which has been reported with a chiral copper catalyst[4a] and more successfully with a rhodium catalyst that was mediated by a chiral sulfur ylide.[4b] A third strategy arises from the recent observation that simple Lewis acids can catalyze formation of aziridines from ethyl diazoacetate and imines.[5,6] However, a screen of this reaction with a variety of chiral Lewis acids failed to produce aziridines with significant asymmetric induction.[5c]

Scheme I

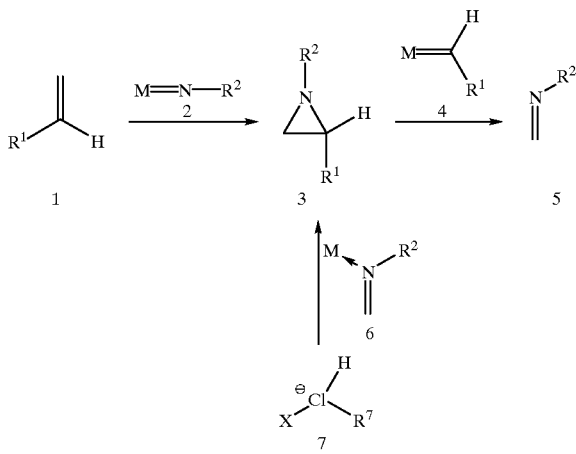

Despite these advances, there remains a need for a process for producing chiral aziridines.

BRIEF SUMMARY OF THE INVENTION

Accordingly, one aspect of the present invention is a process for producing chiral cis-aziridines.

These and other aspects of this invention, which will become apparent during the course of the following detailed description of the invention, have been discovered by the inventors. That is, the present inventors have discovered that a chiral vaulted biaryl-Lewis Acid complex can give very high asymmetric inductions in the formation of aziridines from the reaction of an imine (I) with a diazo compound (II).

DETAILED DESCRIPTION OF THE INVENTION

I. Definitions

"Alkyl" (or alkyl- or alk-) refers to a substituted or unsubstituted, straight, branched or cyclic hydrocarbon chain containing of from 1 to 20 carbon atoms. Preferred alkyl groups are lower alkyl groups, i.e., alkyl groups containing from 1 to 6 carbon atoms. Preferred cycloalkyls have from 3 to 10, preferably 3–6, carbon atoms in their ring structure. Suitable examples of unsubstituted alkyl groups include methyl, ethyl, propyl, isopropyl, cyclopropyl, butyl, iso-butyl, tert-butyl, sec-butyl, cyclobutyl, pentyl, cyclopentyl, hexyl, cyclohexyl, and the like.

"Alkenyl" refers to a substituted or unsubstituted, straight, branched or cyclic, unsaturated hydrocarbon chain that contains at least one double bond and 2 to 20, preferably 2 to 6, carbon atoms. Exemplary unsubstituted alkenyl groups include ethenyl (or vinyl)(—CH=CH$_2$), 1-propenyl, 2-propenyl (or allyl)(—CH$_2$—CH=CH$_2$), 1,3-butadienyl (—CH=CHCH=CH$_2$), 1-butenyl(—CH=CHCH$_2$CH$_3$), hexenyl, pentenyl, 1,3,5-hexatrienyl, and the like. Preferred cycloalkenyl groups contain five to eight carbon atoms and at least one double bond. Examples of cycloalkenyl groups include cyclohexadienyl, cyclohexenyl, cyclopentenyl, cycloheptenyl, cyclooctenyl, cyclohexadienyl, cycloheptadienyl, cyclooctatrienyl and the like.

"Alkoxy" refers to a substituted or unsubstituted, —O-alkyl group. Exemplary unsubstituted alkoxy groups include methoxy, ethoxy, n-propoxy, isopropoxy, n-butoxy, t-butoxy, and the like.

"Alkynyl" refers to a substituted or unsubstituted, straight, branched or cyclic unsaturated hydrocarbon chain containing at least one triple bond and 2 to 20, preferably 2 to 6, carbon atoms.

"Aryl" refers to any monovalent aromatic carbocyclic group of 5 to 10 carbon atoms. The aryl group can be bicyclic (i.e. phenyl (or Ph)) or polycyclic (i.e. naphthyl) and can be unsubstituted or substituted.

"Amine" refers to an unsubstituted or substituted amino group. The amine can be primary (—NH$_2$), secondary (—NHR) or tertiary (—NR$_2$), where R is a substituent. Examples of substituted amino groups include methylamino, dimethylamino, ethylamino, diethylamino, 2-propylamino, 1-propylamino, di(n-propyl)amino, di(iso-propyl)amino, methyl-n-propylamino, t-butylamino, and the like.

"Halogen" (or halo-) refers to fluorine, chlorine, iodine or bromine. The preferred halogen is fluorine or chlorine.

"Heterocyclic" (Het or heterocyclyl) refers to a stable, saturated, partially unsaturated, or aromatic group containing 5 to 10, preferably 5 or 6, ring atoms. The ring can be substituted 1 or more times with a substituent. The ring can be mono-, bi- or polycyclic. The heterocyclyl group consists of carbon atoms and from 1 to 3 heteroatoms independently selected from the group consisting of nitrogen, oxygen, and sulfur. Examplary heterocyclyl groups include acridine, benzathiazoline, benzimidazole, benzofuran, benzothiapene, benzthiazole, benzothiophenyl, carbazole, cinnoline, furan, imidazole, 1H-indazole, indole, isoindole, isoquinoline, isothiazole, morpholine, oxazole (i.e. 1,2,3-oxadiazole), phenazine, phenothiazine, phenoxazine, phthalazine, piperazine, pteridine, purine, pyrazine, pyrazole, pyridazine, pyridine, pyrimidine, pyrrole, quinazoline, quinoline, quinoxaline, thiazole, 1,3,4-thiadiazole, thiophene, 1,3,5-triazines, triazole (i.e. 1,2,3-triazole), and the like.

"Inert atmosphere" refers to reaction conditions in which the mixture is covered with a layer of inert gas such as nitrogen or argon.

"Protecting group" refers to a group used to protect a heteroatom such as oxygen, nitrogen, sulfur or phosphorus from chemical reaction. For example, a O-protecting group is used to protect an oxygen heteroatom, such as in a hydroxy group, from reaction. Examples of O-protecting groups include t-butoxycarbonyl (Boc), t-butyl ether, benzyl ethers, and the like. Examples of N-protecting groups include carbobenzoyl (Cbz), fluorenylmethyloxycarbonyl (FMOC), nitropiperonyl, pyrenylethoxycarbonyl, nitroveratryl (NV), nitrobenzyl, and the like. Protecting groups are well known in the art, see for example, Protective Groups in Organic Synthesis, Peter G. M. Wuts (Editor), Theodora W. Greene, 3rd ed. (April 1999), Vch Pub.; Protective Groups in Organic Synthesis, Theodora W. Greene, Peter G. Wuts (Contributor), 2nd ed., (May 1991) John Wiley & Sons. Preferred protecting groups include, but are not limited to, the "Boc" protecting group, trialkyl silyl groups such as TBS (tert-butyldimethylsilyl, $Si(CH_3)_2C(CH_3)_3$), MEM, MOM, SEM, and THP.

"Substituted" means that the moiety contains at least one, preferably 1–3 substituent(s). Suitable substituents include hydrogen and hydroxyl, amino, oxy (—O—), thio (—S—), thiol, alkyl, alkenyl, alkynyl, halo, nitrile, nitro, silyl, aryl and heterocyclyl groups. These substituents can optionally be further substituted with 1–3 substituents. For example, substituted substituents include alkoxy, carbonyl, esters, ketones, carboxylic esters, sulfonyl, thionyl, carboxamide, alkylmercapto, alkylsulphonyl, alkylamino, dialkylamino, carboxylate, alkoxycarbonyl, alkylaryl, aralkyl, alkylheterocyclyl, and the like.

All other acronyms and abbreviations have the corresponding meaning as published in journals relative to the art of chemistry.

II. Process of the Present Invention

The process of the present invention comprises reacting an imine (I) with an diazo compound (II) in the presence of a catalyst to form a cis-aziridine product (III).

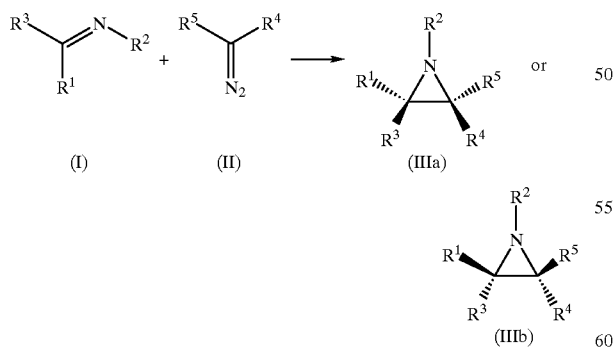

Imine (I) can be commercially obtained. Alternatively, such imines can be formed via a variety of known chemical reactions (See e.g. March, Advanced Organic Chemistry: Reactions, Mechanisms, and Structure, $3^{rd}$ ed., John Wiley & Sons: New York, p. 1165, 1985).

In imine (I):

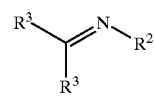

$R^1$ is hydrogen, substituted carbonyl, halo, secondary amino, tertiary amino, nitrile, nitro, alkyl, alkenyl, alkynyl, alkoxy, aryl or heterocyclyl groups. $R^1$ is preferably hydrogen, alkyl, alkenyl, alkynyl, alkoxy, aryl or heterocyclyl groups. $R^1$ is most preferably hydrogen. When $R^1$ is substituted, the substituent should not chemically interfere with the process of the present invention (i.e., typically hydroxy, primary amino, and thiol groups are not used as substituents).

$R^2$ is hydrogen, hydroxyl, amino, oxo, carbonyl, thiol, halo, nitrile, nitro, alkyl, alkenyl, alkynyl, alkoxy, aryl or heterocyclyl groups. $R^2$ is preferably an alkylaryl or aryl group. $R^2$ is most preferably phenyl, benzyl or benzhydryl (—CH(Ph)$_2$). When $R^2$ is substituted, the substituent should not chemically interfere with the process of the present invention.

$R^3$ is hydrogen, substituted carbonyl, halo, secondary amino, tertiary amino, nitrile, nitro, alkyl, alkenyl, alkynyl, alkoxy, aryl or heterocyclyl groups. $R^3$ is preferably alkyl, aryl or heteroaryl. $R^3$ is most preferably phenyl. When $R^3$ is substituted, the substituent should not chemically interfere with the process of the present invention (i.e., typically hydroxy, primary amino, and thiol groups are not used as substituents).

Diazo compound (II) can be commercially obtained. Alternatively, diazo compound (II) can be formed via a variety of known chemical reactions (See e.g. Diazo compounds: Properties and Synthesis, Manfred Regitz and Gerard Maas, Academic Press, 1986, Orlando, Fla.).

In the diazo compound (II):

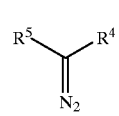

$R^4$ and $R^5$ are each independently hydrogen (H), secondary amino (—NHR), tertiary amino, substituted oxo, substituted carbonyl, thiol, halo, nitrile, nitro, substituted silyl, alkyl, alkenyl, alkynyl, alkoxy, aryl or heterocyclyl groups. $R^4$ is preferably a substituted carbonyl (particularly ester or ketone) or silyl group. $R^5$ is preferably a hydrogen, alkyl, alkenyl, alkynyl, aryl or heterocyclyl group.

In the formed cis-aziridine product (III):

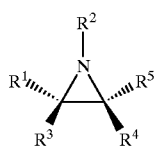

(IIIb)

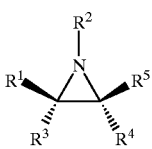

R[1], R[2], R[3], R[4], and R[5] are as defined above. The configuration of the cis product is determined by the catalyst which is used. The cis-product (IIIa) is obtained from catalyst (IVa), shown below. It should be understood that the other cis-product (IIIb) can be obtained using catalyst (IVb).

The process of the present invention comprises reacting an imine (I) with an diazo compound (II) in the presence of a catalyst to form a cis-aziridine product (III).

The catalyst used in the process of the present invention is preferably a chiral vaulted biaryl-Lewis Acid complex of the formulae (IVa or IVb):

(IVa)

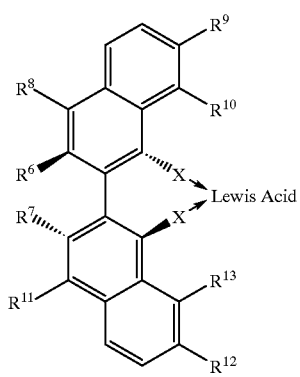

(IVb)

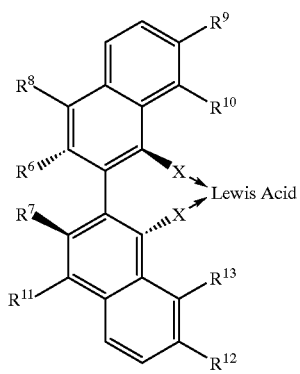

In each of formulae (IV), X is N, O or S. X is preferably O.

R[6] and R[7] are each independently an alkyl, aryl or heterocycyl group. These substituents preferably prevent rotation around the bond connecting the two aryl systems, typically through steric hindrance. Preferably, R[6] and R[7] are both unsubstituted or substituted phenyl. When substituted, the aryl group is preferably substituted at the para-position.

R[8], R[9], R[10], R[11], R[12], and R[13], are each independently hydrogen, alkyl, aryl, and heterocyclyl. Alternatively, R[6] and R[8], R[7] and R[11], R[9] and R[10], and R[12] and R[13] can, each pair independently, form a fused aliphatic or aromatic ring. A preferred aromatic ring is phenyl. Preferably, each pair of R[9] and R[10], and R[12] and R[13], forms a phenyl ring.

A preferred chiral vaulted biaryl catalyst is vaulted 3,3'-biphenanthrol (VAPOL) (see formula (IVc)).

(IVc)

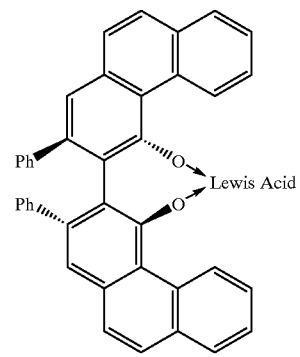

Chiral vaulted biaryl catalysts can be produced as described in the scientific literature, (See e.g., "The Synthesis, Resolution and Determination of Absolute Configuration of a Vaulted 2,2'-Binaphthol and a Vaulted 3,3'-Biphenanthrol (VAPOL)," Bao et al., J. Am. Chem. Soc., 1996, 118: 3392–3405).

Lewis acids which are complexed to the catalyst of the present invention include any compound which can act as an electron pair acceptor and can catalyze the aziridine reaction in the absence of the chiral vaulted biaryl catalyst (i.e., the racemic aziridine reaction). Examples include $BX_3$, $AlX_3$, $FeX_3$, $SnX_4$, $SiX_4$, $ZnX_2$, $LiX$, $MgX_2$, $TiX_4$, and $ZrX_4$, where each X is independently hydrogen, alkyl, aryl, heterocycyl or alkoxy. Preferably, at least one X in the Lewis acid is hydrogen.

When the chiral vaulted biaryl-catalyst is VAPOL, then the preferred Lewis acid is $BX_3$, most preferably $BH_3$.

Chiral vaulted biaryl-Lewis Acid complexes can be formed by heating the chiral vaulted 3,3'-biarylanthrol in the presence of a solution of the Lewis acid.

The order of the reactants in the process of the present invention is not critical. However, the inventors have found that the rate of reaction is fastest when the imine (I) is slowly added to a solution containing the diazo compound (II) and the catalyst (IV). The reaction will proceed, albeit slower, when the diazo compound (II) is added to a solution containing the imine (I) and the catalyst (IV).

The molar ratio of imine (I): diazo compound (II) is preferably from about 1:1 to about 1:1.5, most preferably about 1:1.1. The amount of catalyst (IV) used in the process of the present invention is typically from about 1 to 10 mol % of imine (I), preferably about 2.5 mol %.

The process of the present invention is preferably conducted in an organic solvent. Most preferably, the process is conducted in a substantially anhydrous organic solvent. Suitable organic solvents include any non-aqueous solvent, e.g. halogenated hydrocarbons (such as methylene chloride ($CH_2Cl_2$), chloroform ($CH_3Cl$), carbon tetrachloride ($CCl_4$)), toluene, xylene, benzene, dimethyl sulfoxide (DMSO), dimethylformamide (DMF), sulfolane, tetrahydrofuran (THF), diethyl ether ($Et_2O$), methyl-t-butyl ether, and 1,2-dimethoxyethane. Preferably, organic solvents which can not coordinate to the chiral vaulted biaryl catalyst are used.

The process of the present invention is preferably conducted for ≧5 minutes, preferably from about 20 minutes to 24 hours. The process is preferably conducted at a temperature of from about 0 to 60° C., most preferably about ambient temperature. The process is preferably conducted under an inert atmosphere (such as argon or nitrogen).

The aziridine product (III) can be purified from the reaction mixture using conventional means, e.g. precipitation, chromatography, and the like. The aziridine products (III) produced by the process of the present invention are typically stable and can be stored.

The process of the present invention yields the cis-aziridine product (III) with an enantiomeric excess of $\geq 85\%$, preferably $\geq 90\%$, more preferably $\geq 95\%$, most preferably $\geq 97\%$, as determined by HPLC using a Chiralcel OD column (available from Diacel Chemical Industries, Ltd.).

The process of the present invention is highly diastereoselective for the formation of cis-aziridine product (III) with $\geq 30:1$, preferably $\geq 40:1$, most preferably $\geq 50:1$ cis to trans selectivity.

The aziridines produced by the process of the present invention are highly strained systems, rendering them susceptible to ring-opening reactions, and, in turn, making them useful as substrates, auxiliaries, reagents, and ligands in the field of stereoselective synthesis.[1] Aziridines also have been shown to exhibit potent biological activity, which is intimately associated with the reactivity of the strain heterocycle.[2]

EXAMPLES

Materials and Methods

All experiments were performed under an argon atmosphere. Flasks were flame-dried and cooled under argon before use. Methylene chloride and toluene were distilled from calcium hydride under nitrogen. Hexanes and ethyl acetate were ACS grade and used as purchased. Reagents were purified by simple distillation or recrystallization with appropriate solvents. Imines were purified by recrystallization from absolute ethanol or pentane/methylene chloride mixtures. Ethyl diazoacetate was used as purchased from Aldrich except in one case of purification by column chromatography. Borane-THF was used as purchased from Aldrich. VAPOL was purified by column chromatography with 9:1 hexanes:ethyl acetate. All aldimines were synthesized by a known procedure.[13] Aziridines were purified by column chromatography with hexanes/ethyl acetate and further by recrystallization from pentane/methylene chloride if desired.

Melting points were determined on a Hoover Unimelt apparatus and are not corrected. IR spectra were taken on a Nicolet 20SX FTIR instrument. $^1$H and $^{13}$C NMR spectra were recorded on a Bruker 400 MHz or a Bruker 500 MHz instrument in $CDCl_3$ unless otherwise noted. $CDCl_3$ was also used as the internal standard for both $^1$H NMR ($\delta$=7.24) and $^{13}$C NMR ($\delta$=77.0). Low-resolution mass spectra and high-resolution mass spectra were performed at the University of Illinois, Urbana, Ill. Elemental analysis were performed by Galbraith Laboratories, Inc., Knoxville, Tenn. Analytical thin-layer chromatography (TLC) was performed on Merck silica gel plates with F-254 indicator. Visualization was by long wave ultraviolet light, exposure to iodine vapor, or by staining with p-anisaldehyde in ethanol/sulfuric acid or phosphobolybdic acid in ethanol. Flash column chromatography was performed with E. Merck silica gel 60 (230–400 mesh).

HPLC was carried out using a Waters M-45 Solvent Delivery System equipped with a Waters Model U6K Universal Liquid Chromatograph Injector, a Waters Model 440 Absorbance detector, and a Spectra-Physics Chromjet Integrator. Chiral HPLC data was obtained through the use of a Diacel Chiralcel OD column.

Optical rotations were obtained on a Perkin-Elmer 141 polarimeter at a wavelength of 589 nm (sodium D line) using a 1.0 decimeter cell with a total volume of 1.0 mL. Specific rotations are reported in degrees per decimeter at 23° C. and the concentrations are given in grams per 100 mL in methylene chloride.

A typical experimental procedure for the synthesis of all aldimines: Aldehydes and N-diphenylmethylamine were distilled before use. Solid aldehydes were used as purchased from Aldrich. The N-diphenylmethylamine was typically dissolved in 50 mL of $CH_2Cl_2$ for each 30 mmol of amine. To this stirred flask, a quantity of 4 g of $MgSO_4$ was added. After 10 min. of stirring, the same 30 mmol quantity of aldehyde was added slowly by syringe. The reaction was stirred from 4 to 16 hours while being monitored by TLC for loss of starting material. Upon completion the reaction contents were gravity filtered and concentrated by rotary evaporation to give the crude imine 8a–8g, and 8i as crude solids. These were then recrystalized from EtOH and in one case from pentane:$CH_2Cl_2$. Imine 8h was a liquid at room temperature and was used without further purification. All imine yields were from 60–88 % after a single crop upon recrystallization.

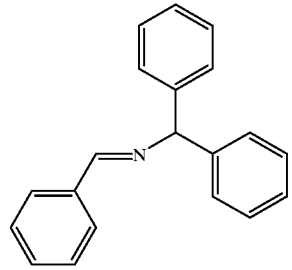

(8a)

N-Benzylidene-1,1-diphenylmethylamine (8a)[14] White crystal.

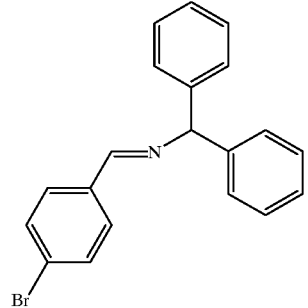

(8b)

N-(4-Bromobenzylidene)-1,1-diphenylmethylamine (8b)[15] White crystal.

(8c)

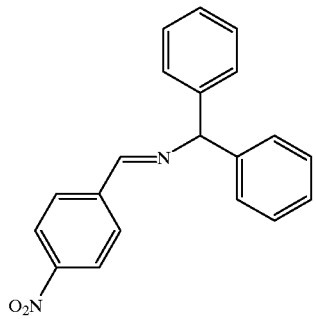

N-(4-Nitrobenzylidene)-1,1-diphenylmethylamine (8c)[15] Off-white crystal.

(8d)

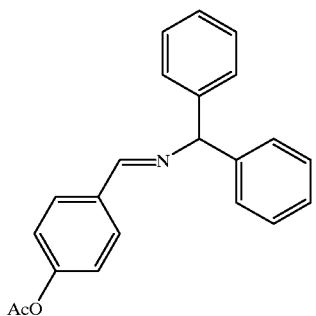

N-(4-Acetoxybenzylidene)-1,1-diphenylmethylamine (8d) [16] White crystal.

(8e)

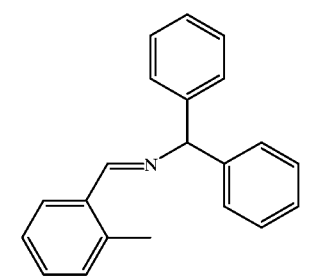

N-(o-Tolylbenzylidene)-1,1-diphenylmethylamine (8e) White crystal.

(8f)

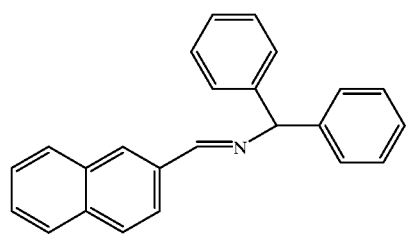

N-(2-Naphthylidene)-1,1-dipenylmethylamine (8f) White crystal.

(8g)

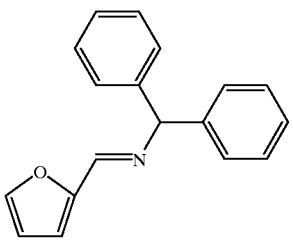

N-(Furan-2-ylmethylidine)-1,1-diphenylmethylamine (8g) [14] White crystal, (8h)

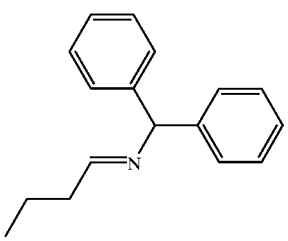

N-Propylidine-1,1-diphenylmethylamine (8h) Light yellow oil.

(8i)

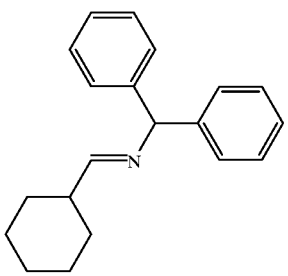

N-(Cyclohexylmethylidene)-1,1-diphenylmethylamine (8i) [14] White crystal.

Experimental procedure to form the boron-VAPOL catalyst (14) To a flame-dried Schlenk flask cooled under argon was added 54 mg of S or R-VAPOL (0.10 mmol) which was dissolved in 2 mL of $CH_2Cl_2$. To this flask 300 µL of 1M $BH_3$-THF (0.30 mmol) was added. This stirred mixture was heated to 55° C. for 1 hour and then a vacuum (0.5 mm Hg) was applied for one-half hour with continual heating at 55° C. The catalyst 14 was then used by dissolving in appropriate solvent and transferring to reaction flask.

(10a)

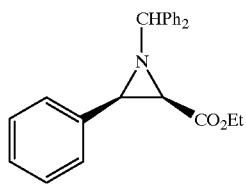

A typical asymmetric aziridination procedure for cis-aziridines : Cis-1-(N-1,1-diphenylmethyl)-(2R)-carboxyethyl-(3R)-phenylaziridine (10a) The catalyst 14 from 54 mg (0.10 mmol) of S-VAPOL was dissolved in 1 mL of toluene and transferred via syringe to a 10 mL flame dried flask with stir bar at room temperature. To this flask was first added 115 μL (1.1 mmol) of ethyl diazoacetate by syringe. After five minutes of stirring, 271 mg (1.00 mmol) of imine 8a in 1 mL of toluene was added via syringe pump addition over 3 hours. Two additional hours of stirring were allowed before the reaction contents were diluted with 10 mL of ethyl ether and washed twice with 20 mL portions of brine. The organic layer was dried over $MgSO_4$, gravity filtered, and concentrated by rotary evaporation to give the crude aziridine as a off-white solid. The cis/trans ratios were found by comparing the $^1H$ NMR integration values for the relative aziridine methine protons. The cis (7–8 Hz) and the trans (2–3 Hz) coupling constants were used to differentiate the two isomers. Acyclic enamine products (11a–i, 12a–i) were also determined by $^1H$ NMR of the crude reaction mixture with the N—H proton integration relative to the integration of the aziridine methine protons. The solid crude reaction mixture was purified by column chromatography (50 mm column, 6" $SiO_2$, 9:1 hexanes:ethyl acetate) to give aziridine 10a as a white solid (275 mg) in 77% isolated yield. An optical purity of 97% ee was determined by HPLC analysis using a chiralcel OD column with 9:1 hexanes:2-propanol as the eluent, flow rate=1.0 mL/min. The respective racemic aziridine was made with $BF_3$-$Et_2O$ as the catalyst[17] under similar reaction conditions for confirmation of retention times. Retention times: $t_r$=5.4 min (minor enantiomer) and $t_r$=10.5 min (major enantiomer) were found by chiral HPLC. Cis/trans ratio: >50:1. Side products: <1% 11a and <1% 12a. White solid. Specific rotation: $[\alpha]^{23}_D$=+38.2° C=2 ($CH_2Cl_2$).

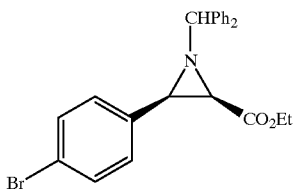

(10b)

Cis-1-(1,1-diphenylmethyl)-(2R)-carboxyethyl-(3R)-(p-Bromophenyl)-aziridine (10b) The same procedure as with 10a was followed with these changes: 350 mg (1.00 mmol) of Imine 8b was dissolved in 3 mL of toluene and added to 54 mg (0.10 mmol) of the S-VAPOL derived catalyst 14/ethyl diazo acetate mixture in 1 mL of toluene. The reaction stopped 1 hour after the 3 hour syringe pump addition (reaction time 4 hours). The product was a white solid (278 mg) in 64% isolated yield and an optical purity of 97% ee, Cis/trans ratio: 16:1. Side products: 2.0% 11b and 3.9% 12b. Chiral HPLC: $t_r$=5.3 min (minor isomer) and $t_r$=11.2 min (major isomer). White solid, mp 150–151° C. (hex/EtOAc). Specific rotation: $[\alpha]^{23}_D$=+10.9° C=2 ($CH_2Cl_2$).

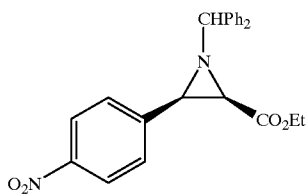

(10c)

Cis-1-(1,1-diphenylmethyl)-(2R)-carboxyethyl-(3r)-(p-Nitrophenyl)-aziridine (10c) The same procedure as with 10a was followed with the these changes: 316 mg (1.00 mmol) of imine 8c was dissolved in 2 mL toluene and added to the catalyst 14 derived from 54 mg (0.10 mmol) of S-VAPOL in 1 mL of toluene with 115 μL (1.1 mmol) of ethyl diazoacetate at 0° C. After 3 hours of syringe pump addition of the imine at 0° C. the reaction was warmed back to room temperature and stirred for another 21 hours (24 hr reaction time). An isolated yield of 68% (272 mg) was found with an optical purity of 91% ee. Cis/trans ratio: 11:1, Side products: <1% 11c and <1% 12c. Chiral HPLC: $t_r$=9.0 min (minor isomer) and $t_r$=12.2 min (major isomer). Off-white solid, mp 133–135° C. (hex/EtOAc). Specific Rotation: $[\alpha]^{23}_D$=–10.0° C=1 ($CH_2Cl_2$).

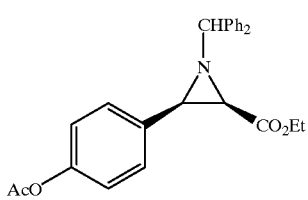

(10d)

Cis-1-(N-1,1-diphenylmethyl)-(2R)-carboxyethyl-(3R)-(p-acetoxyphenyl)-aziridine (10d) The same procedure as with 10a was followed with the these changes: 329 mg (1.00 mmol) of imine 8d was added in 1 mL of toluene by syringe pump for 3 hours to the 54 mg (0.10 mmol) of S-VAPOL derived catalyst 14/ethyl diazoacetate 1.15 μL (1.1 equ.) mixture in 1 mL of toluene at room temperature. The reaction was stirred for another 13 hours to completion (16 hour reaction time). An isolated yield of 67% (278 mg) with a 96% ee was found. Cis/trans ratio: 40:1. Side products: 3.6% 11d and 3.0% 12d. Chiral HPLC retention times: $t_r$=7.5 min (minor isomer) and 10.9 min (major isomer). White solid, mp 148–150° C. (hex/EtOAc). Specific rotation: $[\alpha]^{23}_D$=+29.9° C=1 ($CH_2Cl_2$).

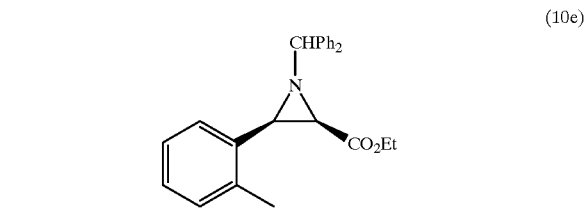

(10e)

Cis-1-(N-1,1-diphenylmethyl)-(2R)-carboxyethyl-(3R)-(o-tolyl)-aziridine (10e) The same procedure as with 10a was followed with the these changes: Imine 8e, 607 mg (2 mmol), was added in 4 mL of toluene by 3 hour syringe pump addition to the 54 mg (0.10 mmol) of S-VAPOL derived catalyst 14/ethyl diazoacetate 230 µL (2.2 mmol) mixture in 1 mL of toluene at room temperature (5 mol % in catalyst). The reaction was allowed to stir for another 21 hours to completion (24 hr reaction time). The reaction gave 784 mg of 10e as a white solid in 51% yield and an optical purity of 98% ee. Cis/trans ratio: 3:1. Side products: 8.1% 11e and 6.5% 12e. Chiral HPLC: $t_r$=6.7 min (minor isomer) and $t_r$=8.5 min (major isomer) with 40:1 hexanes:2-propanol as the eluent. mp 162–163° C. (hex/EtOAc). Specific rotation: $[\alpha]^{23}_D$=+37.0° C.=2 ($CH_2Cl_2$).

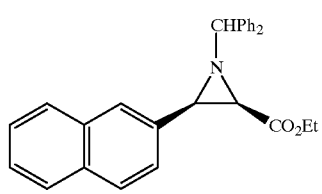
(10f)

Cis-1-(1,1-diphenylmethyl)-(2R)-carboxyethyl-(3R)-2'-naphthylaziridine (10f) The same procedure as with 10a was followed with the these changes: Imine 8f, 321 mg (1.00 mmol), was dissolved in 1 mL of $CH_2Cl_2$ and added by syringe pump over 3 hours to the 27 mg of S-VAPOL (0.050 mmol) derived catalyst 14/ethyl diazoacetate 115 µL (1.1 mmol) mixture in 1 mL of $CH_2Cl_2$ at room temperature. The reaction was stopped 1 hour later (4 hour reaction time) to provide the title compound in a 70% isolated yield (285 mg) with an optical purity of 97% ee. Cis/trans ratio: 30:1. Side products: 1.5% 11f and 1.4% 12f. Chiral HPLC: $t_r$=5.5 min (minor isomer) and 10.9 min (major isomer). White solid; m.p. 150–153° C. (hex/EtOAc). Specific rotation: $[\alpha]^{23}_D$=−6.9° C=1 ($CH_2Cl_2$).

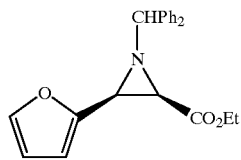
(10g)

Cis-1-(1,1-diphenylmethyl)-(2R)-carboxyethyl-(3R)-(2'-furyl)-aziridine (10g) The same procedure as with 10a was followed with the these changes: Imine 8g, 261 mg (1.00 mmol), was dissolved in 4 mL of toluene and added by syringe pump over 3 hours to the 54 mg of (0.10 mmol) S-VAPOL derived catalyst 14/ethyl diazoacetate 115 µL (1.1 mmol) mixture at room temperature. The reaction was stopped 5 hours later (8 hour reaction time) and a 55% yield of 10g (191 mg) was obtained with an optical purity of 94.5% ee. Cis/trans ratio: 16:1. Side products: <1% 11g and <1% 12g. Chiral HPLC: $t_r$=5.2 min (minor isomer) and $t_r$=11.8 min (major isomer). White solid, m.p 104–105° C. (hex/EtOAc). Specific rotation: $[\alpha]^{23}_D$=+7.1° C=1 ($CH_2Cl_2$).

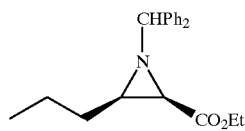
(10h)

Cis-1-(1,1-diphenylmethyl)-(2R)-carboxyethyl-(3R)-n-propylaziridine (10h) The same procedure as with 10a was followed with the these changes: Imine 8h, 237 mg (1.00 mmol), was dissolved in 1 mL of toluene and added by syringe pump over 3 hours to the 54 mg (0.10 mmol) of S-VAPOL derived catalyst 14/ethyl diazoacetate 115 µL (1.1 mmol) mixture at 0° C. The reaction was allowed to warm to room temperature and stopped 4 hours later (7 hour reaction time) and a 54% yield (128 mg) of 10h was obtained with an optical purity of 91% ee. Cis/trans ratio: >50:1. Side products: 9.6% 11h and 6.4% 12h. Chiral HPLC: $t_r$=4.9 min (minor isomer) and $t_r$=10.4 min (major isomer). White solid, mp 104–105° C. (hex/EtOAc). Specific rotation: $[\alpha]^{23}_D$=+89.5° C=1 ($CH_2Cl_2$).

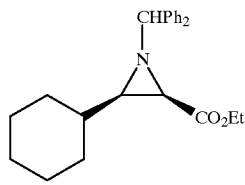
(10i)

Cis-1-(1,1-diphenylmethyl)-(2R)-carboxyethyl-(3R)-cyclohexylaziridine (10i) The same procedure as with 10a was followed with the these changes: Imine 8i, (1.00 mmol) was dissolved in 1 mL of toluene and added by syringe pump over 2 hours to the 54 mg (0.10 mmol) of the S-VAPOL derived catalyst 14/ethyl diazoacetate 115 µL (1.1 mmol) mixture at room temperature. The reaction was stopped 1 hour after the slow addition (3 hour reaction time) and a 72% yield (261 mg) of 10i was obtained with an optical purity of 96% ee. Cis/trans ratio: 35:1. Side products: <1% 11i and <1% 12i. Chiral HPLC: $t_r$=9.9 min (minor isomer) and $t_r$=16.72 min (major isomer) with 40:1 hexanes:2-propanol as the eluent. White solid, mp 162.5–163° C. (hex/EtOAc); Specific rotation: $[\alpha]^{23}_D$=+137.3° C.=1 ($CH_2Cl_2$).

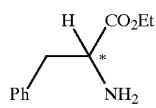
(15a)

Procedure for the hydrogenation of 10a to give D-phenyl alanine ethyl ester (15a)[18] Aziridine 10a with 97% ee was recrystallized once from $CH_2Cl_2$/pentane (1:15) to give a white cotton-like solid which was determined to be 99.2% ee by chiral HPLC. This enriched 10a, 125 mg (0.50 mmol) was then dissolved in a 5 mL solution of formic acid (5 v/v %) in methanol and added via cannula to 0.016 g (0.15 mmol) of palladium black in 0.5 mL of the 5% formic acid/methanol solution. The reaction stirred for 24 hours and was worked-up by gravity filtration, rotary evaporation and stirring in 25 mL saturated carbonate solution for 1 hour followed by partitioning into two successive 20 mL methylene chloride extractions. The organic layers were combined, dried over MgSO$_4$, and reduced by rotary evaporation to give the crude amino acid ethyl ester. This ester was purified by column chromatography on SiO$_2$ with acetonitrile:MeOH 20:1 as the eluent. Compound 15a was found in an 80% yield (54 mg) as a colorless oil. Specific rotation found: $[\alpha]^{23}_D=-23.0°$ C=3.2 (EtOH). Literature[19] rotation: $[\alpha]^{23}_D=+23.8°$ C=3.2 (EtOH) for L-phenyl alanine ethyl ester.

Results

Very high asymmetric inductions can be achieved with a catalyst prepared from VAPOL and borane-tetrahydrofuran complex. This catalyst was prepared by treating VAPOL with 3 equivalents of borane-THF complex and heating at 55° C. for one hour, removal of volatiles and then heating the residue at 55° C. for 30 minutes under a high vacuum.[8] Entry 4 in Table 1 shows that this catalyst produces a 74% yield of the aziridine 10a in 98% ee along with a dramatically reduced level of acyclic products. The cis aziridine is produced with a distereoselectivity of greater than 50:1 with the catalyst generated from VAPOL but this falls to 8:1 with the catalyst prepared from BINOL. In addition the enantiomeric excess with the BINOL catalyst falls to 17% ee.

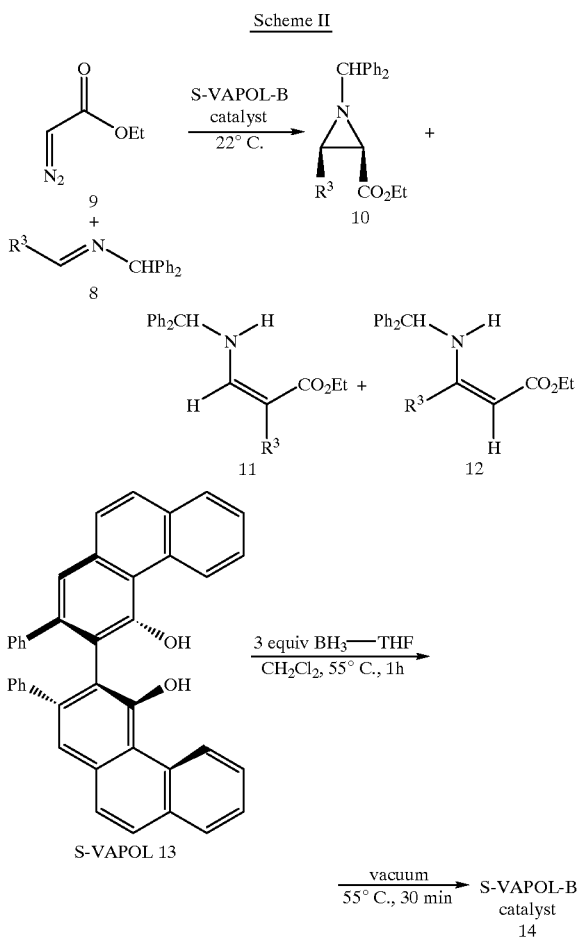

Scheme II

The asymmetric induction observed for 10a is not a function of the substrate to catalyst ratio and remains constant as the catalyst loading is reduced from 10 to 1 mole % (entries 5–9). The rate of the reaction significantly drops when the amount of catalyst is reduced from 10 to 2.5 mole percent, but interestingly, the rate of the reaction is greatly accelerated if the imine is added by slow addition. Entries 7 and 8 reveal that the order of addition of reagents does not affect the rate. However, the data in entries 7 and 9 reveal that the reaction time can be reduced from 20 hours to 2 hours for reactions with 2.5 mol % catalyst if the imine is added over a period of one hour. The reactions in Tables 1 and 2 were performed with imines that were crystallized from ethanol.[9] Imine 8a contained traces of ethanol as revealed by $^1$H NMR but this was only found to be detrimental to the rate with very low catalyst loadings. More reasonable reaction times were observed with 1 mol % catalyst when the imine was purified by crystallization from pentane/CH$_2$Cl$_2$. The effect of ethanol was confirmed when the reaction in entry 10 of Table I was repeated in the presence of 10 mol % ethanol and found to proceed only to the extent of 18% conversion in 17 hours.

TABLE 1

Asymmetric Aziridination of Imine[8a] with S-VAPOL-Boron Catalyst[14,a]

| Entry | Catalyst (mol %) | Time, h | Yield cis[10b] | % ee cis[10c] | Cis[10]/trans[10d] | Yield[11e] | Yield[12e] |
| --- | --- | --- | --- | --- | --- | --- | --- |
| 1 | 10 | 20 | 42[f] | 17 | 8:1 | 8 | 10 |
| 2 | 10 | 20 | 53[g] | 66 | >50:1 | 13 | 6 |
| 3 | 10 | 18 | 41 | 5 | >50:1 | 17 | 14 |
| 4 | 10 | 0.5 | 74 | 98 | >50:1 | 2 | 2 |
| 5 | 10 | 0.5 | 78[ij] | 97 | >50:1 | 2.5 | 2.1 |
| 6 | 5 | 3 | 74 | 97.5 | >50:1 | 1.7 | 0.7 |
| 7 | 2.5 | 20 | 73 | 97 | >50:1 | 1–1.5 | 1–1.5 |
| 8 | 2.5[k] | 17 | 74 | 97 | >50:1 | 1.6 | 1.0 |
| 9 | 2.5[l] | 2 | 79 | 98 | >50:1 | ≦1 | ≦1 |
| 10 | 1[l] | 16[m] | 72 | 99 | 42:1 | 3.7 | 2.5 |

[a]Unless otherwise specified, all reactions were run in methylene chloride with 0.1 mmol of S-VAPOL at 22° C. with 1.1 equivalent of ethyl diazoacetate with respect to imine[8,9] was added all at once to a mixture of limine and catalyst. Imine[8] was crystallized from ethanol and[9] was used as supplied by Aldrich. Imine concentration is 0.5M for entries 1–6 and 2.0M for entries 7–10.
[b]Isolated after purification by silica gel chromatography.
[c]Determined by HPLC on a Chiralcel OD column.
[d]Determined by $^1$HNVR of crude reaction mixture.
[e]Determined by $^1$HNVR of crude reaction mixture by integration relative to cis[10].
[f]Catalyst prepared from R-BINOL and BH$_3$-THF which gave the enantiomer of[10a].
[g]Catalyst prepared from S-VAPOL and BH$_2$Br-Me$_2$S.
[h]Catalyst prepared from S-VAPOL and Et$_2$AlCl.
[i]Reaction with R-VAPOL which gave the enantiomer of[10a].
[j]80% recovery of VAPOL.
[k]Imine added all at once to a mixture of catalyst and[9].
[l]Imine added over 3 h by syringe pump to a mixture of the catalyst and[9].
[m]Imine crystallized from CH$_2$Cl$_2$/hexane.

This asymmetric aziridination reaction was found to be slightly faster in methylene chloride than in toluene, although the latter solvent in some cases gave higher inductions for the cis- aziridine and less of the acyclic products 11 and 12. For this reason, the scope of the reaction was explored in toluene for the substrates listed in Table 2. As can be seen, high enantioselectivities were observed over a range of imine substrates derived from both electron-rich and electron-poor aryl aldehydes and with branched and unbranched aliphatic aldehydes.[10] The reaction times shown in Table 2 are not reflective of rate differences in the imine substrates since the concentrations varied due to solubility and since minimum reaction times were not determined. It was observed that the p-bromo and p-nitro substituted imines 8b and 8c are more reactive than the phenyl imine 8a under the same conditions. The imine prepared from p-methoxy benzaldehyde was slower than imine 8a and did go to completion in methylene chloride in 24 hours but the aziridine was not stable to purification on silica gel.

TABLE 2

Asymmetric Aziridination of Imine 8 with S-VAPOL-Boron Catalyst 14.[a]

| Entry | Imine | R³ | Time, h | Yield cis 10[b] | % ee cis 10[c] | Cis 10/ trans 10[d] | Yield 11[e] | Yield 12[e] |
|---|---|---|---|---|---|---|---|---|
| 1 | 8a | Ph | 5 | 77 | 97 | >50:1 | ≦1 | ≦1 |
| 2 | 8b | p-BrC₆H₄ | 4 | 64 | 97 | 16:1 | 3.9 | 2.0 |
| 3 | 8c | p-NO₂C₆H₄ | 24 | 68[f] | 91 | 11:1 | ≦1 | <1 |
| 4 | 8d | p-OAcC₆H₄ | 16 | 67 | 96 | 40:1 | 3.6 | 3.0 |
| 5 | 8e | o-MeC₆H₄ | 24 | 51[i] | 98 | 3:1 | 8.1 | 6.5 |
| 6 | 8f | 2-Naphthyl | 4 | 70[g,h,i,j] | 97 | 30:1 | 1.5 | 1.4 |
| 7 | 8g | 2-furyl | 8 | 55 | 94.5 | 16:1 | ≦1 | ≦1 |
| 8 | 8h | n-Propyl | 7 | 54[f] | 91 | >50:1 | 9.6 | 6.4 |
| 9 | 8i | c-C₆H₁₁ | 3 | 72 | 96 | 35:1 | ≦1 | ≦1 |

[a]Same as footnote a in Table 1 except solvent is toluene, 10 mol % catalyst is used and imine is added by syringe pump over 3 hours. Imine concentration varies from 0.20–0.50M.
[b–e]See Table 1.
[f]Reaction started at 0° C. and warmed to RT after 4–5 h.
[g]CH₂Cl₂ as solvent and 5 mol % catalyst.
[h]0.05 mole of VAPOL.
[i]5 mol % catalyst used.
[j]Substrate 9 added all at once to a mixture of catalyst and imine.

The absolute configuration of aziridine 10a was confirmed by reductive ring-opening to phenyl alanine ethyl ester. Transfer hydrogenation with formic acid lead to selective reduction of the nitrogen-benzyl carbon bond of the aziridine and also to the cleavage of the benzhydryl protecting group on the nitrogen to give the ethyl ester of phenyl alanine. The rotation of this material was found to be $[\alpha]_D = -23.0$ (c=3.2, EtOH) which is to be compared with the value of $[\alpha]_D = +23.8$ (c=3.2, EtOH) reported for L-phenyl alanine ethyl ester[11] and which is consistent with the fact that the aziridine 10a used for this reaction was determined to be 99.2% ee by HPLC with a Chiralcel OD column.[12]

PUBLICATIONS CITED 1) a) Tanner, D., *Angew. Chem. Int. Ed. Engl.*, 1994, 33, 599. b) Pearson, W. H.; Lian, B. W.; Bergmeier, S. C., in *Comprehensive Heterocyclic Chemistry II*, Padwa, A., Ed., Pergamon Press, Oxford, 1996, Vol IA, pp 1–60. c) Rai, K. M. L.; Hassner, A., in *Comprehensive Heterocyclic Chemistry II*, Padwa, A., Ed., Pergamon Press, Oxford, 1996, Vol 1A, pp 61–96.

2) Sweeney, J.; Osborn, H. M. I., *Tetrahedron Asym.* 1997, 8, 1693.

3) a) Evans, D. A.; Woerpel, Hinman, M. M.; Faul, M. M., *J. Am. Chem. Soc.*, 1991, 113, 726. b) Lowenthal, R. E.; Masamune, S.; *Tetrahedron Lett.*, 1991, 32, 7373, c) Li, Z.; Conser, K. R.; Jacobsen, E. N., *J. Am. Chem. Soc.*, 1993, 115, 5326. d) Evans, D. A.; Faul, M. M.; Bilodeau, M. T.; Anderson, B. A.; Barnes, D. M., *J. Am. Chem. Soc.*, 1993, 115, 5328. e) Noda, K.; Hosoya, N.; Irie, R.; Ito, Y.; Katsuki, T., *Synlett*, 1993, 469. f) Evans, D. A.; Faul, M. M.; Bilodeau, M. T., *J. Am. Chem. Soc.*, 1994, 116, 2742. g) Tanner, D.; Andersson, P. G.; Harden, A.; Somfai, P., *Tetrahedron Lett.*, 1994, 35, 4631. h) Li, Z.; Quan, R. W.; Jacobsen, E. N., *J. Am. Chem. Soc.*, 1995, 117, 5889. i) Nishikori, H.; Katsuki, T., *Tetrahedron Lett.*, 1996, 37, 9245. j) Harm, A. M.; Knight, J. G.; Stemp, *Synlett*, 1996, 677. k) Muller, P.; Baud, C.; Jacquier, Y.; Moran, M.; Nageri, I.; *J. Phys. Org. Chem.*, 1996, 9, 341. l) Lai, T.-S.; Kwong, H.-L.; Che, C.-M.; Peng, S.-M., *Chem. Commun.*, 1997, 2373. m) Sodergren, M. J.; Alonso, D. A.; Andersson, P. G.; *Tetrahedron: Asymmetry*, 1997, 8, 3563.

4) a) Hansen, K. B.; Finney, N. S.; Jacobsen, E. N., *Angew. Chem. Int. Ed. Engl.*, 1995, 34, 676. b) Rasmussen, K. G.; Jorgensen, K. A., *J. Chem. Soc., Chem. Commun.*, 1995, 1401. c) Aggarwal, V. K.; Thompson, A.; Jones, R. V. H.; Standen, M. C. H., *J. Org. Chem.*, 1996, 61, 8368.

5) a) Casarrubios, L.; Perez, J. A.; Brookhart, M.; Templeton, J. L., *J. Org. Chem.*, 1996, 61, 8358. b) Ha, H.-J.; Kang, K.-H.; Suh, J.-M.; Ahn, Y.-G., *Tetrahedron Lett.*, 1996, 37, 7069. c) Rasmussen, K. G.; Jorgensen, K. A., *J. Chem. Soc., Perkin Trans*, 1, 1997, 1287.

6) For other approaches, see: a) Aires-de-Sousa, J.; Lobo, A. M.; Probhakar, S., *Tetrahedron Lett.*, 1996, 37, 3183. b) Verstappen, M. M. H.; Ariaans, G. J. A.; Zwanenburg, B., *J. Am. Chem. Soc.*, 1996, 118, 8491.

7) a) Bao, J.; Wulff, W. D.; Rheingold, A. L., *J. Am. Chem. Soc.* 1993, 115, 3814. b) Bao, J.; Wulff, W. D., *Tetrahedron Lett.* 1995, 36, 3321. c) Bao, J.; Wulff, W. D.; Dominy, J. B.; Fumo, M. J.; Grant, E. B.; Rob, A. C.; Whitcomb, M. C.; Yeung, S.-M.; Ostrander, R. L.; Rheingold, A. L., *J. Am. Chem. Soc.* 1996, 118, 3392. d) Heller, D. P.; Goldberg, D. R.; Wulff, W. D., *J. Am. Chem. Soc.*, 1997, 119, 10551.

8) The same selectivity is observed with a catalyst prepared with 1.0 equivalents of borane-THF complex but catalyst formation requires longer periods of time.

9) The imines 8a–8i were prepared[13] by reaction of benzhydryl amine with 1.0 equivalent of aldehyde in methylene chloride at room temperature in the presence of anhydrous magnesium sulfate. After filtration, the solvent is removed and the imine purified by crystallization from ethanol with the exception of 8h which is an oil and was used without purification.

10) Imines derived from pivaldehyde and 1-naphthylaldehyde would not undergo reaction under the conditions in Table 2.

11) O'Connor, M. J.; Ernst, R. E.; Schoenberrn, J. E.; Holm, R. H., *J. Am. Chem. Soc.*, 1968, 1744.

12) The aziridine 10a can be improved from 97.0% ee to 99.2% ee with one crystallization.

13) Armesto, D.; Ortiz, M. J.; Perez-Ossoria, R., *J. Chem. Soc., Perkin Trans I*, 1986, 2021.

14) Cainelli et al., *J. Org. Chem.*, 1996, 61, 5134–5139.

15) Green et al., *Tetrahedron*, 1994, 50, 5099–5108.

16) Ishihara et al., *J. Am. Chem. Soc.*, 1994, 23, 10520–10524.

17) Casarrubois et al., *J. Org. Chem.*, 1996, 61, 8358–8359.

18) Lopez et al., *Tetrahedron*, 1996, 52, 8365–8386.

19) O'Conner et al., *J. Am. Chem. Soc.*, 1968, 1744.

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing a chiral cis-aziridine of the formula (IIIa) or (IIIb)

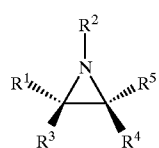

(IIIa)

-continued (IIIb)

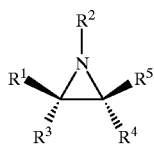

where:

R[1] is hydrogen, substituted carbonyl, halo, secondary amino, tertiary amino, nitrile, nitro, alkyl, alkenyl, alkynyl, alkoxy, aryl or heterocyclyl groups;

R[2] is hydrogen, hydroxyl, amino, oxo, substituted carbonyl, thiol, halo, nitrile, nitro, alkyl, alkenyl, alkynyl, alkoxy, aryl or heterocyclyl groups;

R[3] is hydrogen, substituted carbonyl, halo, secondary amino, tertiary amino, nitrile, nitro, alkyl, alkenyl, alkynyl, alkoxy, aryl or heterocyclyl groups;

R[4] and R[5] are each independently hydrogen, secondary amino, tertiary amino, substituted oxo, substituted carbonyl, thiol, halo, nitrile, nitro, substituted silyl, alkyl, alkenyl, alkynyl, alkoxy, aryl or heterocyclyl groups;

comprising reacting an imine of the formula (I):

(I)

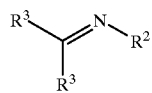

where R[1], R[2] and R[3] are defined above, with a diazo compound of the formula (II):

(II)

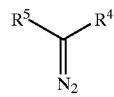

where R[4] and R[5] are defined above, in the presence of a chiral vaulted biaryl-Lewis acid complex of the formula (IVa) or (IVb):

(IVa)

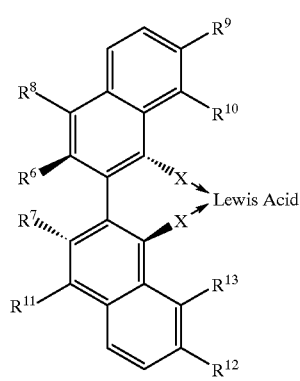

(IVb)

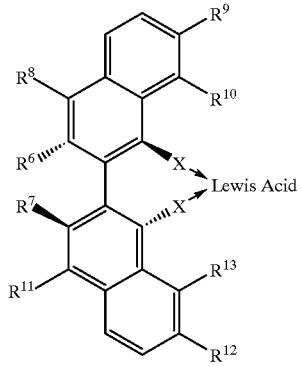

where X is N, O or S;

R[6] and R[7] are each independently an alkyl, aryl or heterocycyl group; and

R[8], R[9], R[10], R[11], R[12], and R[13] are, each independently, hydrogen, alkyl, aryl, and heterocyclyl; or where R[6] and R[8], R[7] and R[11], R[9] and R[10], and R[12] and R[13] may, each pair independently, form a fused aliphatic or aromatic ring;

wherein cis-aziridine (IIIa) is obtained when catalyst (IVa) is employed or wherein cis-aziridine (IIIb) is obtained when catalyst (IVb) is employed.

2. The process of claim 1, wherein R[1] is hydrogen.

3. The process of claim 1, wherein R[2] is phenyl, benzhydryl, or benzyl.

4. The process of claim 1, wherein R[3] is phenyl.

5. The process of claim 1, wherein R[4] is a substituted carbonyl or substituted silyl group.

6. The process of claim 1, wherein R[5] is hydrogen.

7. The process of claim 1, wherein R[6] and R[7] are both phenyl.

8. The process of claim 1, wherein the Lewis acid is $BX_3$, $AlX_3$, $FeX_3$, $SnX_4$, $SiX_4$, $ZnX_2$, $LiX$, $MgX_2$, $TiX_4$, and $ZrX_4$, where each X is independently hydrogen, alkyl, aryl, heterocycyl or alkoxy.

9. The process of claim 1, wherein the Lewis acid is $BH_3$.

10. The process of claim 1, wherein the vaulted biaryl catalyst is (IVc)

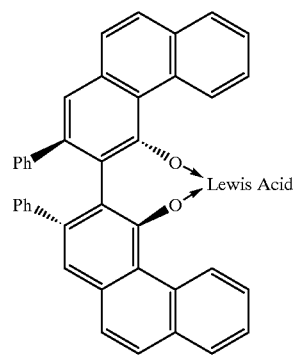

11. The process of claim 10, wherein the Lewis acid is $BX_3$, where each X is independently hydrogen, alkyl, aryl or heterocycyl.

12. The process of claim 11, wherein at least one X is hydrogen.

13. The process of claim 1, wherein the reaction is conducted at a temperature of from about 0 to 60° C.

14. The process of claim 1, wherein the reaction is conducted under an inert atmosphere.

15. The process of claim 1, wherein the reaction is conducted in an organic solvent.

16. The process of claim 15, wherein the organic solvent is substantially anhydrous.

17. The process of claim 1, wherein the reaction is conducted for a time from about 20 minutes to 24 hours.

18. A chiral vaulted biaryl-Lewis acid complex of the formula (IVa) or (IVb):

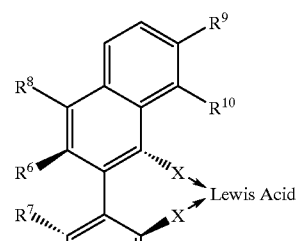

(IVa)

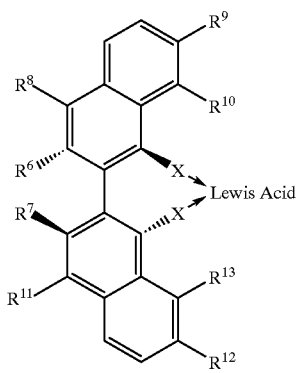

(IVb)

where X is N, O or S;

$R^6$ and $R^7$ are each independently an alkyl, aryl or heterocycyl group;

$R^8$, $R^9$, $R^{10}$, $R^{11}$, $R^{12}$, and $R^{13}$ are, each independently, hydrogen, alkyl, aryl, and heterocyclyl; or where $R^6$ and $R^8$, $R^7$ and $R^{11}$, $R^9$ and $R^{10}$, and $R^{12}$ and $R^{13}$ can, each pair independently, form a fused aliphatic or aromatic ring; and the Lewis acid is $BX_3$, $AlX_3$, $FeX_3$, $SnX_4$, $SiX_4$, $ZnX_2$, $LiX$, $MgX_2$, $TiX_4$, and $ZrX_4$, where each X is independently hydrogen, alkyl, aryl, heterocycyl or alkoxy, provided that at least one X is hydrogen.

19. The complex of claim 18, wherein X is O.

20. A chiral vaulted biaryl-Lewis acid complex of the formula (IVc):

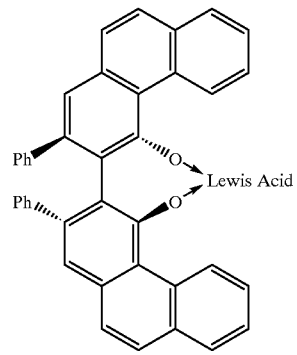

(IVc)

where the Lewis acid is $BX_3$, $AlX_3$, $FeX_3$, $SnX_4$, $SiX_4$, $ZnX_2$, $LiX$, $MgX_2$, $TiX_4$, and $ZrX_4$, where each X is independently hydrogen, alkyl, aryl, heterocycyl or alkoxy, provided that at least one X is hydrogen.

* * * * *